US011534080B2

(12) United States Patent
Apostolos et al.

(10) Patent No.: US 11,534,080 B2
(45) Date of Patent: Dec. 27, 2022

(54) VITAL SIGN MONITORING VIA TOUCHSCREEN USING BIOELECTRIC IMPEDANCE

(71) Applicant: AMI Research & Development, LLC, Windham, NH (US)

(72) Inventors: John T. Apostolos, Lyndeborough, NH (US); William Mouyos, Windham, NH (US)

(73) Assignee: AMI Research & Development, LLC, Merrimack, NH (US)

( * ) Notice: Subject to any disclaimer, the term of this patent is extended or adjusted under 35 U.S.C. 154(b) by 872 days.

(21) Appl. No.: 16/416,442

(22) Filed: May 20, 2019

(65) Prior Publication Data

US 2019/0269349 A1 Sep. 5, 2019

Related U.S. Application Data

(63) Continuation of application No. 15/687,109, filed on Aug. 25, 2017, now abandoned.
(Continued)

(51) Int. Cl.
*A61B 5/00* (2006.01)
*A61B 5/08* (2006.01)
(Continued)

(52) U.S. Cl.
CPC .............. *A61B 5/0809* (2013.01); *A61B 5/01* (2013.01); *A61B 5/021* (2013.01); *A61B 5/0507* (2013.01);
(Continued)

(58) Field of Classification Search
CPC ......... A61B 5/0809; A61B 5/01; A61B 5/021; A61B 5/0507; A61B 5/0531; A61B 5/0816; A61B 5/14532; A61B 5/25; A61B 5/447; A61B 5/4875; A61B 5/6826; A61B 5/6898; A61B 5/742; A61B 5/7475; A61B 5/318; A61B 2562/0214; A61B 2562/046
(Continued)

(56) References Cited

U.S. PATENT DOCUMENTS 4,016,868 A * 4/1977 Allison .................. A61B 5/282
600/388
5,353,793 A * 10/1994 Bornn .................. A61B 5/1135
600/386
(Continued)

OTHER PUBLICATIONS

Braun et al., "Capacitive Proximity Sensing in Smart Environments" Journal of Ambient Intelligence and Smart Environments, (Jul. 2015).
(Continued)

*Primary Examiner* — May A Abouelela
(74) *Attorney, Agent, or Firm* — David J. Thibodeau, Jr.; VLP Law Group LLP

(57) ABSTRACT

Methods and apparatus for detecting body vital signs through the use of a Bioelectric Impedance Spectroscopy (BIS), either by (a) direct contact with the person (such as through one or more of their fingers) or (b) measurement of reflections from a field projected into the person's body. The techniques may be implemented using the projected capacitive touch array in a device such as the screen of a smartphone or tablet computer, or the touchpad of a laptop computer.

10 Claims, 2 Drawing Sheets

Related U.S. Application Data

(60) Provisional application No. 62/379,959, filed on Aug. 26, 2016.

(51) Int. Cl.
| | | |
|---|---|---|
| *A61B 5/0507* | (2021.01) | |
| *A61B 5/0531* | (2021.01) | |
| *A61B 5/25* | (2021.01) | |
| *A61B 5/01* | (2006.01) | |
| *A61B 5/021* | (2006.01) | |
| *A61B 5/145* | (2006.01) | |
| *A61B 5/318* | (2021.01) | |

(52) U.S. Cl.
CPC .......... *A61B 5/0531* (2013.01); *A61B 5/0816* (2013.01); *A61B 5/14532* (2013.01); *A61B 5/25* (2021.01); *A61B 5/447* (2013.01); *A61B 5/4875* (2013.01); *A61B 5/6826* (2013.01); *A61B 5/6898* (2013.01); *A61B 5/742* (2013.01); *A61B 5/7475* (2013.01); *A61B 5/318* (2021.01); *A61B 2562/0214* (2013.01); *A61B 2562/046* (2013.01)

(58) Field of Classification Search
USPC .......................................................... 600/547
See application file for complete search history.

(56) References Cited

U.S. PATENT DOCUMENTS

| | | | | |
|---|---|---|---|---|
| 5,771,891 | A * | 6/1998 | Gozani | A61B 5/14532 600/347 |
| 6,595,918 | B2 * | 7/2003 | Gopinathan | A61B 5/6806 600/300 |
| 6,930,608 | B2 * | 8/2005 | Grajales | A61B 5/0507 340/573.5 |
| 7,112,175 | B2 * | 9/2006 | Gopinathan | A61B 5/0002 600/508 |
| 8,271,079 | B2 | 9/2012 | Cha et al. | |
| 9,524,697 | B2 * | 12/2016 | Ningrat | G06F 3/044 |
| 9,595,918 | B2 | 3/2017 | Li et al. | |
| 9,665,213 | B2 * | 5/2017 | Christman | A61B 5/6897 |
| 9,722,303 | B2 | 8/2017 | Hsieh et al. | |
| 9,723,997 | B1 * | 8/2017 | Lamego | A61B 5/14551 |
| 9,732,997 | B2 | 8/2017 | Sishtla | |
| 9,770,206 | B2 * | 9/2017 | Ashokan | A61B 5/4872 |
| 10,265,022 | B2 * | 4/2019 | Rauhala | G16H 40/67 |
| 10,292,653 | B2 * | 5/2019 | Eom | A61B 5/742 |
| 10,599,101 | B2 * | 3/2020 | Rothkopf | G06F 3/016 |
| 2002/0161290 | A1 * | 10/2002 | Chance | A61B 5/14551 600/323 |
| 2004/0019292 | A1 | 1/2004 | Drinan et al. | |
| 2004/0254496 | A1 | 12/2004 | Itagaki | |
| 2005/0171451 | A1 | 8/2005 | Yeo | |
| 2005/0192510 | A1 * | 9/2005 | Ohkura | A61B 5/0531 600/547 |
| 2005/0228297 | A1 * | 10/2005 | Banet | A61B 5/021 600/485 |
| 2005/0259850 | A1 | 11/2005 | Shimamura et al. | |
| 2007/0173705 | A1 * | 7/2007 | Teller | G16H 10/60 600/300 |
| 2008/0200776 | A1 * | 8/2008 | Schermeier | A61M 16/0833 600/301 |
| 2008/0306400 | A1 * | 12/2008 | Takehara | A61B 5/0537 600/547 |
| 2010/0168530 | A1 * | 7/2010 | Chetham | A61B 5/0537 600/301 |
| 2011/0066050 | A1 * | 3/2011 | Moon | A61B 5/02125 600/509 |
| 2012/0016210 | A1 | 1/2012 | Kim | |
| 2012/0245439 | A1 * | 9/2012 | Andre | A61B 5/412 600/310 |
| 2013/0215042 | A1 * | 8/2013 | Messerschmidt | A61B 5/6898 345/173 |
| 2013/0310700 | A1 * | 11/2013 | Wiard | A61B 5/742 600/485 |
| 2014/0051941 | A1 * | 2/2014 | Messerschmidt | A61B 5/02416 600/301 |
| 2014/0249431 | A1 * | 9/2014 | Banet | A61B 5/1116 600/485 |
| 2014/0249440 | A1 * | 9/2014 | Banet | A61B 5/746 600/526 |
| 2014/0378787 | A1 * | 12/2014 | Brumback | A61B 5/11 600/301 |
| 2015/0157269 | A1 * | 6/2015 | Lisogurski | A61B 7/00 600/301 |
| 2015/0201884 | A1 | 7/2015 | Ashokan | |
| 2015/0238095 | A1 * | 8/2015 | Lading | A61B 5/0285 600/410 |
| 2015/0265217 | A1 * | 9/2015 | Penders | A61B 5/721 600/301 |
| 2015/0282768 | A1 * | 10/2015 | Luna | A61B 5/02444 600/301 |
| 2015/0297145 | A1 * | 10/2015 | Luna | A61B 5/4866 600/301 |
| 2015/0335288 | A1 * | 11/2015 | Toth | A61B 5/6833 600/373 |
| 2015/0362360 | A1 * | 12/2015 | Kovacs | G01G 19/50 177/245 |
| 2016/0051193 | A1 | 2/2016 | Park | |
| 2016/0058375 | A1 * | 3/2016 | Rothkopf | A61B 5/681 600/301 |
| 2016/0073886 | A1 * | 3/2016 | Connor | A61B 5/6887 600/475 |
| 2016/0073914 | A1 * | 3/2016 | Lapetina | A61B 5/282 600/384 |
| 2016/0095522 | A1 * | 4/2016 | Wiard | A61B 5/021 600/483 |
| 2016/0174870 | A1 * | 6/2016 | Lee | A61B 5/0537 600/547 |
| 2016/0198977 | A1 * | 7/2016 | Eom | A61B 5/02416 600/384 |
| 2016/0249857 | A1 * | 9/2016 | Choi | A61B 5/067 600/547 |
| 2016/0328991 | A1 * | 11/2016 | Simpson | G09B 19/0092 |
| 2017/0000415 | A1 * | 1/2017 | Lapetina | A61B 5/0205 |
| 2017/0367600 | A1 * | 12/2017 | Pemberton | A61B 5/339 |
| 2018/0256044 | A1 * | 9/2018 | Goodman | A61B 5/7239 |

OTHER PUBLICATIONS

International Search Report and Written Opinion of the International Searching Authority, PCT/US2017/48681, dated Nov. 28, 2017.

* cited by examiner

VITAL SIGN MONITORING VIA TOUCHSCREEN USING BIOELECTRIC IMPEDANCE

CROSS REFERENCE TO RELATED APPLICATIONS

This patent application claims priority to a co-pending U.S. Patent Application entitled "Vital Sign Monitoring Via Touchscreen Using Bioelectric Impedance" filed Aug. 25, 2017 and given Ser. No. 15/687,109. The entire contents of that application are hereby incorporated by reference.

BACKGROUND

It is known that Bioelectric Impedance Spectroscopy (BIS) may be used for estimating certain vital signs of a person. BIS is relatively easy to implement in portable equipment, and is relatively lower cost as compared to other methods. BIS involves determining the electrical impedance, or opposition to the flow of electric current, through body tissues. BIS typically measures this impedance at a spectrum of frequencies from which the resistances of extracellular and intracellular volumes may be extrapolated. The measured impedance(s) can then be used to calculate an estimate of fat-free body mass and total body water. BIS techniques have also been suggested for detecting heart rate, blood pressure, electrocardiogram (EKG), glucose levels; detection of respiratory rates, drug levels, hydration, ulcers, temperature and other vital signs may be possible using similar techniques.

As one example, in Anas, M. N., "A Bioimpedance Approach", *IEEE International Conference on Smart Instrumentation Measurement and Applications* (ICSIMA), 25-27 Nov. 2013, pp 1-5 (incorporated by reference herein), it was explained that that the impedance of human skin provides details about the physiological structure and chemical composition of the tissues underneath. Glucose concentration was observed to affect the dielectric properties of cellular membranes, and therefore, changes in the impedance of the blood.

Others have reported BIS techniques for detecting glucose concentration, muscle function, skeletal muscle, condition, and cancer. See:

Quazi D Hussain, "Characterization of physiological glucose concentration using electrical impedance spectroscopy", International Journal of Computer Science, Vol 10, issue 1, January 2013;

Tushar Kanti Bera, "Bioelectrical Impedance Methods for Noninvasive Health Monitoring, A Review", Journal of Medical Engineering, Vol 2014, article ID 381251;

Ingrid Anne P. Nazareth, "Analysis of Blood Glucose using Impedance Techniques", International Journal of Innovative Research in Electrical, Electronics, Instrumentation and control Engineering, Vol 1, Issue 9, December 2013;

I Beberashvili, "Bioimpedance phase angle predicts muscle function", European Journal of Clinical Nutrition, 68, 683-689, June 2014;

Digant Gupta, "Bioelectrical impedance phase angle as a prognostic indicator in breast cancer", BMC Cancer, 2008, 8:249; and Yosuke Yamada, "Comparison of single or multifrequency bioelectrical impedance analysis and spectroscopy for assessment of appendicular skeletal muscle", Journal of Applied Physiology, 115, 812-818, 2013.

BRIEF DESCRIPTION OF THE DRAWINGS

The description below refers to the accompanying drawings, of which.

DETAILED DESCRIPTION OF AN ILLUSTRATIVE EMBODIMENT

Figure 1:
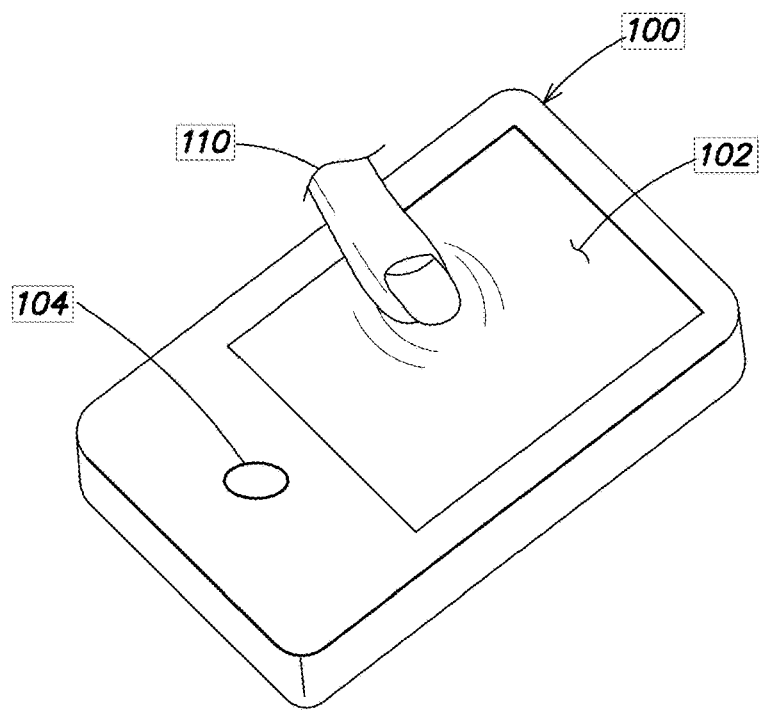
FIG. 1 is an isometric view of a device incorporating a touchscreen which may be used for non-invasive monitoring of vital signs via Bioelectric Impedance Spectroscopy (BIS).

FIG. 1 is an example device 100 such as a smartphone, tablet, computer, video monitor, game console, personal digital assistant, e-book reader or similar information processing apparatus that incorporates a screen having a touch array 102 or similar touch sensitive area such as a trackpad on a laptop computer. In this example, a touch screen includes the touch sensitive array 102 layered over the top of an electronic display. As is well known in the art, the user may use their finger 110 to interact with the touchscreen, and hence touch array 102, provide input to or to control the information processing system. The user may indicate multi-touch gestures by touching or coming in proximity to the touch array 102 with one or more fingers 110. The user can also use the touch array 102 to react to what is displayed and to control how information is displayed.

The touch array 102 (or touchscreen) may be a projected capacitive (pro-cap) type component. Of particular interest to the present discussion is that when a person interacts with such a touch array 102, the underlying sensor array reacts to touches of the person's finger on or near the surface. The touch array 102 includes elements that are disposed as a two-dimensional array or grid. Each sensor element (also referred to as an "intersection" herein) may be implemented as a capacitive sensor connected to a respective position in a grid of wires. However, it should also be understood that the sensor array may not be an actual wire grid but may include capacitive pads that overlap in a diamond pattern, a totem-pole pattern, or other geometric patterns of overlaid conductive elements. What is important is that the sensor array provides a set of intersections arranged along an X and Y axis as a logical grid.

Although not shown here in detail, there are numerous known methods for converting the outputs of a projective capacitive sensor array into a detectable signal, including sensing current versus voltage, phase shifts, resistor-capacitor charge timing, capacitor bridge dividers, charge transfer, successive approximation, sigma-delta modulators, charge accumulation circuits, field-effect, mutual capacitance, frequency shift, many other techniques. The particular method for detecting the relative change in capacitance due to the proximity of a user's finger should be able to detect changes in impedance. More details of an example touch sensor array can be found in U.S. Patent Publication US 2013/0222331 assigned to Cypress Semiconductor, incorporated by reference herein.

Other components of a typical information processing device 100 may include a central processing unit, memory, storage, wireless interfaces, other input devices such as button 104, and other peripheral devices such as cameras, microphones, speakers and the like not shown herein.

Figure 2:
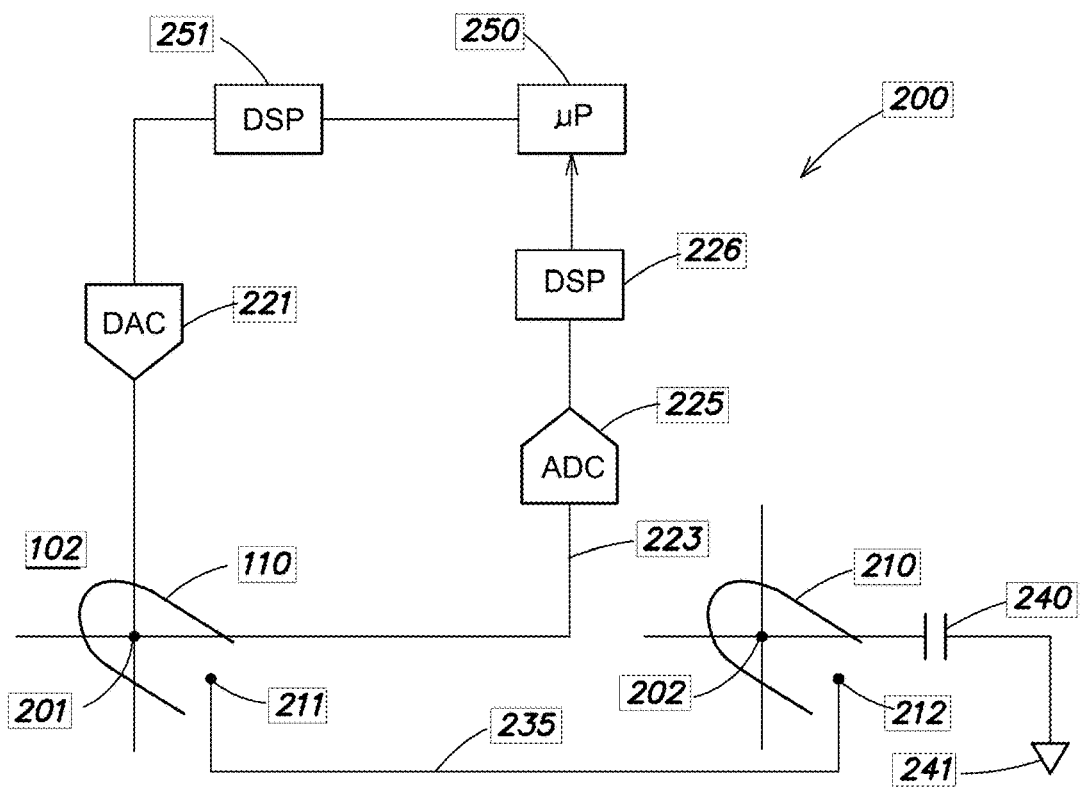
FIG. 2 is an example circuit that may be used with the touchscreen of FIG. 1 for direct impedance measurement.

FIG. 2 shows an example circuit that may be used with the touch array 102 to detect vital signs of person through their finger 110. Circuit 200 includes processor 250 (such as a microprocessor, digital signal processor, controller, or fixed or programmable logic), digital signal processor (DSP) 226, digital-to-analog converter (DAC) 221, and one or more portions of the touch array 102 including at least one or more y-axis grid wires 222 and one or more x-axis grid wires 223, and an analog-to-digital converter (ADC) 225. In one mode of operation, the device 100 through operation of the processor 250 and/or optionally the DSP 251 and DAC 221, imposes a signal on grid wire 222 and an impedance presented by the user's finger 110 is detected at grid wire 223. For example, the processor may cause the DAC 221 to place a signal on the y-axis wire 222 that intersects the finger 110 at grid junction 201. The impedance of the finger 110 affects a current measured via the x-axis line 223, which is then detected by ADC 225 and/or optional DSP 226, and returned as a digital signal to the processor 250. Processor 250 and/or DSP 226 then perform one or more Bioelectric Impedance Spectroscopy (BIS) algorithms to detect the presence of one or more vital signs in the detectable change in impedance signals, using one or more of the aforementioned sensing current versus voltage, phase shifts, resistor-capacitor charge timing, capacitor bridge, charge transfer, successive approximation, sigma-delta modulators, charge accumulation circuits, field-effect, mutual capacitance, frequency shift, etc.

It is the presence of the finger 110 in proximity to the grid intersection 201 that imposes changes in the impedance of, and hence the current flow through, the circuit 200. This measured impedance may then be correlated against a library of known impedances (by the processor 250, for example) for the vital sign(s) of interest. For example, glucose can be measured at frequencies in the range of 50 kHz. The processor 250 and/or DSP 226 may use any known pattern recognition, match filter, Kalmann filter, or other technique for matching responses against patterns of interest. The responses may be stored over time for later analysis. For example, a baseline set of biometrics may be collected for a particular individual on a regular basis. Detection of some deviation from the baseline (such as a relative changes in heart rate, glucose level, blood pressure, EKG, respiratory rates, drug levels, hydration, ulcers, temperature or other vital signs) may cause the processor 250 to provide an indication that the person should seek medical attention.

In this first mode, the impedance measurement can be thought of as a two-port impedance measurement where the transmit line 222 is continuously excited while the response at receive line 223 is measured.

More generally, the signal provided to wire 222 is a radio frequency (RF) signal that may include a sinusoid or other baseband signal from about 0 Hz (DC) to about 100 kHz. It is understood that certain vital signs may involve detection of impedance at more than one frequency. For example, a particular vital sign of interest may involve detecting impedance at three different frequencies. The processor 250 thus may generate the related band or bands of frequencies that include known expected impedance response(s) that characterize that vital sign. The processor 250 may thus generate a series of signals to measure the impedance at a number of frequencies in a time sequence extending over a long period, for example, such as one or more seconds, to detect one or more vital signs. In some implementations, the generated signals may take the form of a continuous linear chirp, where frequency increases (up-chirp) or decreases (down-chirp) over a range of frequencies with time.

The driving signal presented on wire 222 may be a continuous RF signal, or stepped between frequencies of interest, or pulsed, or a continuous linear sweep covering one or more frequency bands of interest.

The specific range of frequencies used may also depend upon the specifications of the available DAC 221 and in ADC 225, as well as anti-aliasing considerations in the resulting signal processing of the signal detected from wire 223.

In a second operating mode, the impedance of not only the one finger 110 but that of other portions of the user's body can be measured. This involves using a second finger 210 placed on another reference point of the device 100 such as on or near a second grid intersection point 202. The second finger may be on the same hand, or on a different hand. The second node 202 is grounded 241 typically through the inter-electrode capacitance 240 of the grid or other capacitance presented by the device 100. The use of two fingers 110 and 210 (or other points) on different hands permits measuring the impedance through a path 235 that includes at least a portion of the user's body, which is applicable to electrocardiogram analysis. A signal propagated through the body in this way may also act as a time domain reflectometer; resulting perturbations in the response signal may provide information as to the relative location of an anomaly in the body. For example, if the BIS operating mode is set to detect the presence of cancerous cells, the relative time difference of arrival may indicate a location of a tumor on the person's body.

It is natural for a person to hold a smartphone in the palm of one hand while interacting with the touchscreen using the other hand. Therefore, the reference point need not necessarily be the finger of the other hand, but can also be another point on the device 100 with a known impedance such as the person's hand or palm contacting or in proximity to a conductive node on the back of the case of the device 100 or some other conductive point on the device 100.

Figure 3:
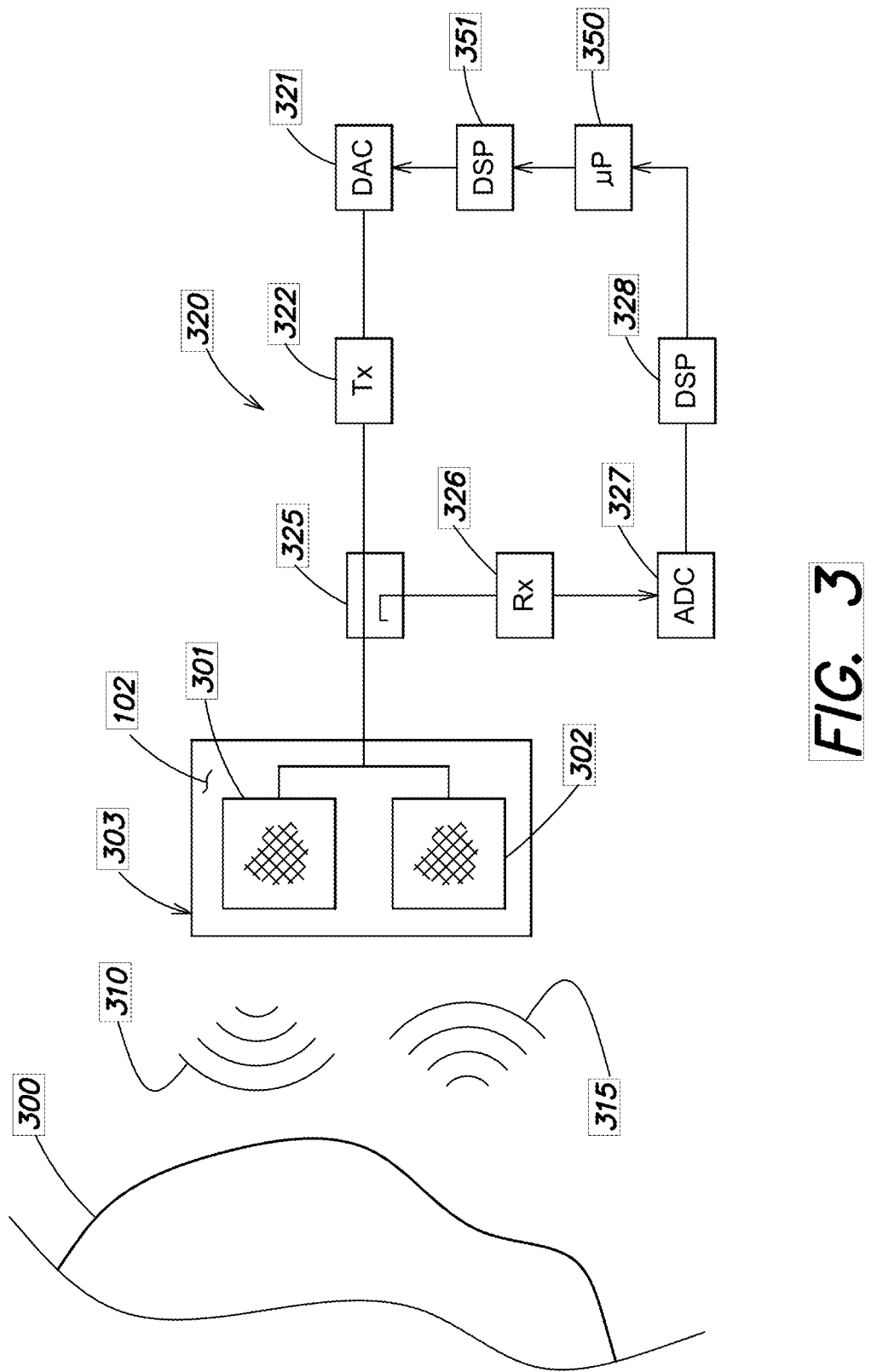
FIG. 3 is a circuit which may be used in another embodiment using a projected field.

FIG. 3 illustrates yet another mode where the touch array 102 may detect vital signs or other conditions through the bioelectric impedance effect via a projected field 310. In this implementation, the projective capacitance array 102 is divided into two portions, a first portion 301 and a second portion 302. Each portion 301, 302 is set in a mode where the respective grid intersection points are all connected together. This in effect creates a pair of radiating surfaces, and thus a dipole antenna 303, through which radio frequency signals may be propagated and detected. Thus, the device 100 can now be used to detect vital signs without even requiring the person to come in physical contact with the touch array 102 with their finger (or other object). In effect, the touch array 102 operates as a dipole radiator 303 to project an RF field 310 that passes through an object 300 such as a person's body (or some other thing such as a liquid, solid, or gas); the same dipole 303 may also be used to detect resulting reflections 315. Although not shown in the drawings, tuning circuits may be included to tune the dipole radiator 303 for efficient operation at the expected frequencies of operation.

The reflection coefficient of the body or other object 300 may contain the same information as detected through the direct contact, bio-electric impedance measurements described above for FIG. 2. The projected field mode of FIG. 3, (or "radar" mode if you will) involves transmitting a radiated signal while receiving a reflection from the object 300. Thus the circuitry 320 used in this mode may be similar to that in a continuous wave (CW), chirp, or other type of radar.

Circuitry 320 includes a microprocessor 350 (or other controller or signal processor), DSP 351, DAC 321, transmitter 322, a directional coupler 325, receiver 326, ADC 327 and DSP 328 (which may or may not be the same machine as DSP 351). In this embodiment, the processor 350 controls the DSP 351 and DAC 321 to generate an analog representation of a signal to be emitted to create the field 310. The transmit signal is then fed to the transmitter 322 (which may include analog filtering circuits) passing through directional coupler 325 and to dipole antenna 303 to create the emitted field 310. In the receive direction the reflected field 315 from the object 300 is detected by the dipole antenna 303, and the resulting signal fed through the directional coupler 325 to receiver 326 (which may include bandpass filters), converted to digital form by ADC 327, and fed to the DSP 328 and/or processor 350 for BIS analysis.

As in the embodiments described above the RF field frequencies of interest will depend upon the particular vital sign(s) of interest and BIS operating mode, and may range from, for example, DC to 100 kHz.

While what is shown is the use of DAC 321 and analog filtering 322, it is understood that direct digital synthesis, digital detection, or other techniques may be used by DSPs 351 and 328 to generate the projected field 310 and detect the response field 315.

In other implementations, it is possible that the dipole antenna 303 may not be implemented with the touch array 102 but rather with a separate metallic radiator. For example, certain smartphones already have a dipole antenna located in the periphery of the case for operating at cellular, Bluetooth, and Global Positioning System (GPS) frequencies. In other implementations, a separate dipole antenna designed specifically for vital sign detection via BIS may be used.

The embodiment of FIG. 3 thus also relies upon a bioelectric impedance effect, albeit with the use of a projected field 310 and the corresponding reflection reflected field 315, rather than through direct contact current measured as in FIG. 2.

In another embodiment, it may be possible to use the same or similar apparatus and methods to detect certain non-biological properties of the body or other substance using techniques other than BIS. More generally, dielectric spectroscopy techniques (sometimes called impedance spectroscopy, and also known as electrochemical impedance spectroscopy (EIS)), may measure the dielectric properties of other media, such as gases, liquids or solids, that are in proximity to the touchscreen. From these reflectance measurements, it may be possible to determine the chemical composition or other characteristics of such other media.

The frequency (wavelength) of the radiated field will typically depend upon the substance of interest. For example, to detect alcohol on someone's breath, or the presence of gluten in a food product, may use other spectroscopy techniques that operate with near-infrared frequencies. Nuclear Quadrupole Resonance (NQR) and Nuclear Magnetic Resonance (NMR) techniques may extend the ability to detect substances from the reflections such as explosives or opiates. Still other methods may pick up physical vibrations in a person's breath from the reflected signals, which can be used to detect other conditions, such as bronchitis.

In still other embodiments, a camera located within the device 100 may be used to aim the dipole antenna 303 formed from the touchscreen at the body 300 or other material to be analyzed.

Various modifications to the embodiments described above will now become apparent. For example, most projective capacitive arrays 102 as used in smartphones already include an ADC 225 of some type, but it may be necessary to augment the standard smartphone circuitry to include a DAC 221 and/or the DSPs and/or antennas or other structures that operate at higher RF frequencies and/or infrared wavelengths.

It is also understood that the processor(s) 250, 350, may typically operate in different modes switching back and forth periodically between a BIS spectroscopy mode and the "normal" touchscreen operating mode (such as to detect user gestures and the like). In such an implementation, the detection of biometrics or other properties of an object may thus occur in the background, under control of an operating system kernel for example, in such a way that the user does not have to run a separate software application.

What is claimed is:

1. An apparatus comprising:
   a touchscreen incorporating a projective capacitive touch array adjacent an electronic display;
   the projective capacitive touch array comprising a two-dimensional grid including a set of first axis wires disposed along a first axis of the grid, and a set of second axis wires arranged along a second axis of the grid;
   a circuit connected to the projective capacitive touch array, to selectively impose an electrical signal on one or more of the first axis wires and detect a resulting response at one or more of the second axis wires, wherein the electrical signal is a continuous radio frequency signal comprising a time sequence of two or more frequencies, or a continuous linear sweep between the two or more frequencies, the two or more frequencies induce a response that characterizes one or more vital signs;
   an analog-to-digital converter connected to the circuit and arranged to convert the resulting response to one or more digital values; and
   a processor for executing stored program instructions to:
   operate a touch gesture process to detect touch gesture inputs from the projective capacitive touch array;
   display information on the electronic display in response to the touch gesture inputs;
   control the circuit to impose the electrical signal;
   receive the one or more digital values from the analog-to-digital converter; and
   execute a Bioelectric Impedance Spectroscopy (BIS) process to determine the one or more body vital signs from the digital values.

2. The apparatus of claim 1 wherein the BIS process further determines one or more impedance values by determining a measure of current, voltage, phase shift, resistor-capacitor charge timing, capacitor bridge, charge transfer, successive approximation, sigma-delta modulators, charge accumulation circuits, field-effect, mutual capacitance, or frequency shift.

3. The apparatus of claim 1 additionally comprising:
   wherein the circuit provides the resulting response as an impedance; and
   wherein the processor is further configured to execute the instructions to:

match the digital values against a library of impedances known to be characteristic of one or more vital signs of interest.

4. The apparatus of claim 1 wherein the two or more frequencies are in a range of up to 100 kHz.

5. The apparatus of claim 1 wherein the processor is further configured to execute the instructions to:
switch back and forth periodically between operating the touch gesture process and operating the BIS spectroscopy process.

6. The apparatus of claim 1 additionally comprising:
a reference node; and
wherein the circuit further provides the resulting response as an impedance relative to the reference node and the two-dimensional grid; and
wherein the one or more digital values are indicative of an impedance of a path through a selected finger of a person located adjacent the two-dimensional grid and a portion of the person's body other than the selected finger disposed adjacent the reference node.

7. The apparatus of claim 6 wherein the processor is further configured to execute the instructions to:
determine a time difference of arrival from the one or more digital values, the time difference of arrival indicative of a relative location of an anomaly.

8. The apparatus of claim 1 wherein the grid is additionally arranged into a first portion and a second portion, to provide a dipole radiator, the dipole radiator projecting a radio frequency (RF) field external to the apparatus in response to the electrical signal, and the resulting response indicative of reflections caused by the projected RF field.

9. The apparatus of claim 8 wherein the electrical signal applied to the dipole radiator is a continuous chirp signal.

10. The apparatus of claim 1 wherein the one or more vital signs are selected from a group consisting of relative changes in heart rate, glucose level, blood pressure, EKG, respiratory rates, drug levels, hydration, ulcers, or temperature.

* * * * *